United States Patent [19]

Bell et al.

[11] Patent Number: 5,010,021

[45] Date of Patent: Apr. 23, 1991

[54] METHOD FOR RESTORING THE SENSING CAPACITY OF AN ELECTRICAL SENSOR

[75] Inventors: William E. Bell; John J. McNerney, both of Jerome, Ariz.

[73] Assignee: Arizona Instrument Corp., Tempe, Ariz.

[21] Appl. No.: 146,419

[22] Filed: Jan. 21, 1988

Related U.S. Application Data

[60] Division of Ser. No. 735,484, May 20, 1985, Pat. No. 4,724,008, which is a continuation-in-part of Ser. No. 529,578, Sep. 6, 1983, abandoned.

[51] Int. Cl.$^5$ ............................................. G01N 27/08
[52] U.S. Cl. ..................... 436/120; 204/432; 204/153.19; 338/34; 422/82.02; 422/83; 422/90; 436/121; 436/122; 436/123
[58] Field of Search ............... 422/68, 90, 83, 82.02; 134/2, 19; 204/1 T, 432; 210/760; 338/34; 436/120-123

[56] References Cited

U.S. PATENT DOCUMENTS

| | | | |
|---|---|---|---|
| 3,714,562 | 1/1973 | McNerney | 422/69 |
| 4,274,970 | 6/1981 | Beitzel | 204/158.2 |
| 4,326,927 | 4/1982 | Stetter et al. | 204/406 |
| 4,351,734 | 9/1982 | Kaufman | 204/302 |
| 4,412,924 | 11/1983 | Feather | 210/760 |

Primary Examiner—Robert J. Warden
Assistant Examiner—Timothy M. McMahon
Attorney, Agent, or Firm—Cahill, Sutton & Thomas

[57] ABSTRACT

A selected component of a fluid mixture, for example a reduced sulfur compound vapor in air, is detected by selectively adsorbing the component onto a conductive thin layer of material having a chemical affinity for such component and observing the resultant change of electrical resistivity of the layer. The sensitivity of the detector changes with accumulation of the component on the sensor. The accumulation of the component on the sensor is removed by oxidizing and evolving the component from the sensor to restore the sensor to a linear operating region. The accumulated component is preferably oxidized by reacting the component with ozone. The dynamic range of the sensor is increased by counteracting the tendency for the component to accumulate by continuously feeding back ozone to or controlling the temperature of the sensor so that the sensor operates in a linear region near null.

4 Claims, 2 Drawing Sheets

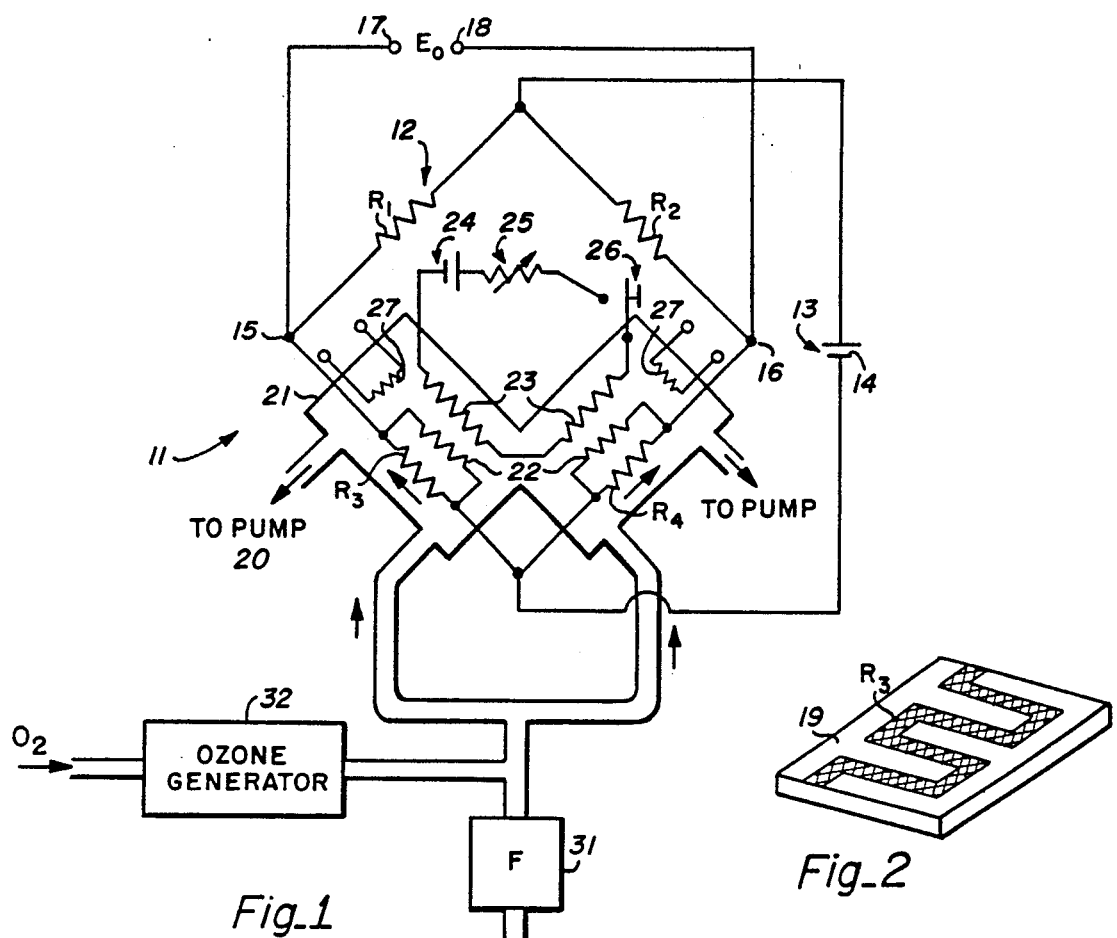
Fig_1
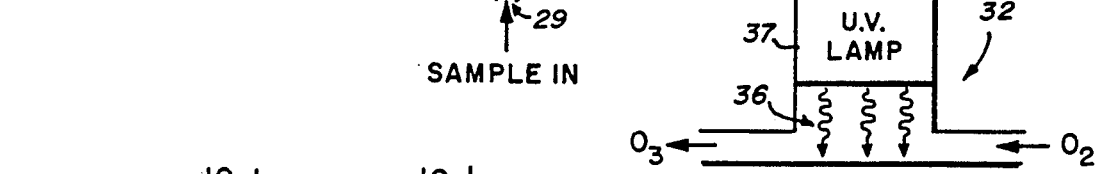
Fig_2
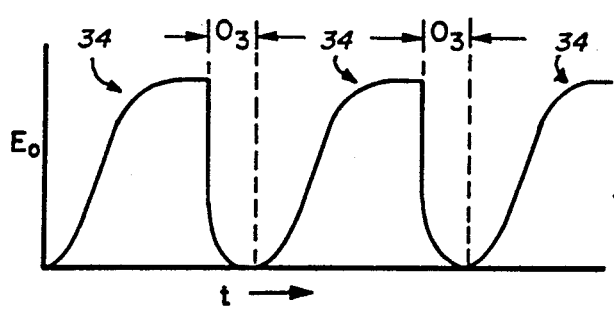
Fig_3
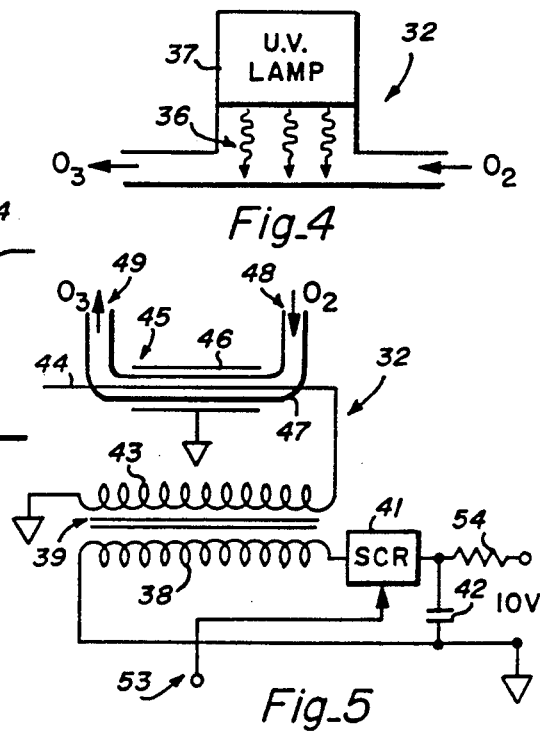
Fig_4
Fig_5

| 5,010,021 |

METHOD FOR RESTORING THE SENSING CAPACITY OF AN ELECTRICAL SENSOR

RELATED CASES

The present application is a divisional application of U.S. application Ser. No. 735,484, filed May 20, 1985, now U.S. Pat. No. 4,724,008, which is a continuation in part application of U.S. patent application Ser. No. 529,578, filed Sept. 6, 1983, now abandoned.

BACKGROUND OF THE INVENTION

The present invention relates in general to method and apparatus for selective detection of components in fluids and, more particularly, to improvements for retaining and restoring the sensing capacity of the sensor which tends to become saturated with accumulation of the component on the sensor.

DESCRIPTION OF THE PRIOR ART

Heretofore, gas detectors have been developed in which a component of a fluid mixture, for example, mercury or hydrogen sulfide vapor in air is detected by selectively adsorbing the component onto an electrically conductive thin layer of a material, such as gold, having an amalgamating or a chemical affinity for such gaseous component and observing the resultant change of electrical resistivity of the layer. Such a gas detector is described and claimed in U.S. Pat. No. 3,714,562 issued Jan. 30, 1973 and further described in an article entitled: "Mercury Detection by Means of Thin Gold Films" appearing in Science, Vol. 178, pgs. 611-612 of Nov. 10, 1972.

One of the difficulties with such a gas detection system is that the selected component adsorbed onto the metallic layer tends to accumulate on the surface. As the accumulation builds up, the sensor tends to saturate, thereby impairing its sensing capacity. Heretofore, when the metallic sensing member approached saturation or non-linearity, it was heated to 150 degrees C. for 10 minutes. This heating evolved the adsorbed mercury, thereby cleaning the film and restoring its former sensitivity. The action that was taking place was the mercury was being evolved or vaporized from the gold layer with which it had amalgamated.

It was also known from the prior art that a gold film could be utilized for sensing hydrogen sulfide vapor. However, heating the gold film to 150 degrees C. did not abruptly expel the sulfur component as was observed with mercury.

It would be desirable if a mechanism could be found for cleaning the surface of the metallic sensor, as in the case of a hydrogen sulfide detector, so as to restore the sensing capacity of the detector.

SUMMARY OF THE PRESENT INVENTION

The principal object of the present invention is the provision of an improved method and apparatus for the detection of reduced sulfur components in fluids and, more particularly, to method and apparatus for cleaning the sensing films of the accumulated sulfur component being detected.

In one feature of the present invention, the accumulated component on the sensor is removed by oxidizing and evolving the sulfur from the sensor for restoring the sensing capacity of the sensor.

In another feature of the present invention, the sensor is cleaned by heating the sensor in contact with oxygen to a sufficient temperature to oxidize and evolve the sulfur from the sensor.

In another feature of the present invention, the accumulated sulfur component on the sensor is oxidized by reacting ozone with the acumulated sulfur component.

In another feature of the present invention, the selected sulfur component to be detected is reacted with the sensor material to produce a first reaction product to effect a change in an electrical parameter of the sensor. A second component is also reacted with the first reaction product to counteract or reverse the change in the electrical parameter produced by the first reaction product. The amount of the second component used to counteract the effect of the first component is used to derive a measure of the sulfur component. Other features and advantages of the present invention will become apparent upon a perusal of the following specification taken in connection with the accompanying drawings wherein:

FIG. 1 is a schematic circuit diagram, partly in block diagram form of an apparatus for detection of selected components in fluids and incorporating features of the present invention, FIG. 2 is a schematic perspective view of a sensor metallic film deposited upon an insulated substrate.

FIG. 3 is a plot of voltage vs. time depicting the cleaning effect of ozone for restoring the sensing capacity of the sensor, FIG. 4 is a schematic line diagram of an ozone generator employed in one embodiment of the present invention, FIG. 5 is a schematic circuit diagram, partly in block diagram form, of an alternative ozone generator useful in the apparatus of the present invention, and FIG. 6 is a schematic block diagram of an alternative gas detection apparatus incorporating features of the present invention.

DESCRIPTION OF THE PREFERRED EMBODIMENTS

Figure 6:
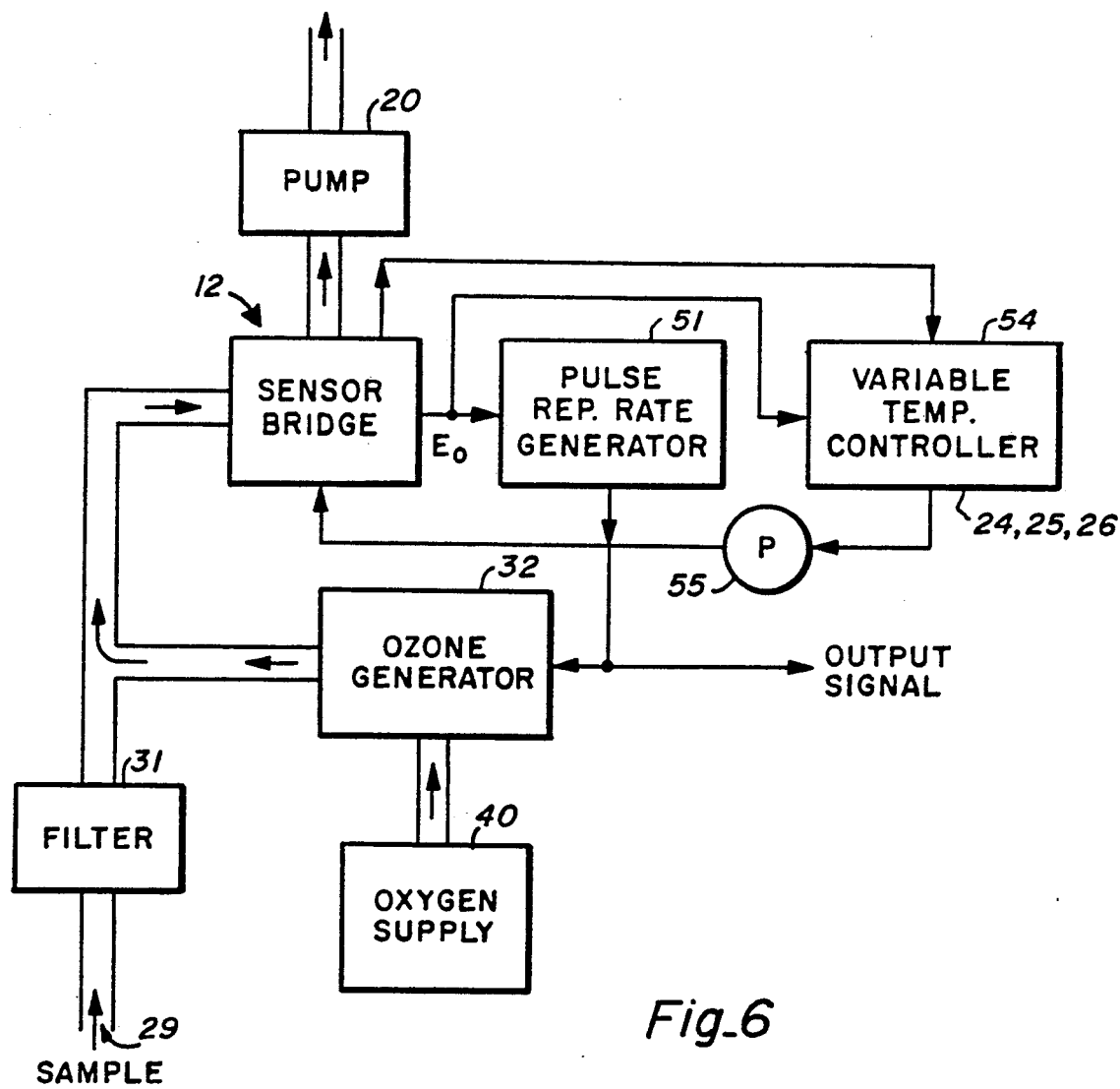

Referring now to FIG. 1, there is shown a gas detection apparatus 11 of the present invention. The apparatus 11 is an improvement of the apparatus disclosed in the aforecited U.S. Pat. No. 3,714,562 the disclosure of which is hereby incorporated by reference in its entirety. The apparatus 11 includes a Wheatstone electrical bridge 12 including four resistors $R_1$, $R_2$, $R_3$, and $R_4$ connected into the conventional Wheatstone bridge configuration. The bridge 12 includes a pair of parallel branches connected across the output of a power source 13, such as battery 14. One of the parallel branches of the circuit includes resistors $R_1$ and $R_3$, whereas the other parallel branch includes resistors $R_2$ and resistor $R_4$. The circuit nodes between the resistors in each of the parallel branches, namely nodes 15 and 16, are connected to the output terminals of the bridge at 17 and 18 respectively.

The value of resistor $R_1$ equals the value of resistor $R_2$ and the value of resistor $R_3$ equals the value of resistor $R_4$. The output $E_0$ at the output terminals 17 and 18 is zero at null or at balance of the bridge. Resistor $R_3$ is chosen as the sensing resistor for sensing the selected gaseous sulfur component. Resistor $R_4$ is made identically to that of resistor $R_3$ with the exception that its surface is passivated so as to render it insensitive to the gaseous sulfur component to be detected. Resistors $R_1$ and $R_2$ are chosen to be of equal value.

Resistor $R_4$, in the absence of any effect due to adsorption of the gaseous sulfur component to be detected, has a value of resistance equal to that of $R_3$ and thus the bridge is balanced and the output $E_0$ is zero at null. However, when a gaseous sulfur component to be detected is adsorbed onto the surface of resistor $R_3$, it changes its electrical resistance thereby unbalancing the bridge and giving a non-zero output signal $E_0$ at output terminals 17 and 18.

In a typical example, resistors $R_3$ and $R_4$ each comprise a thin metallic film resistor such as a film of gold having a thickness, as of 4,000 Å to 8,000 Å (See FIG. 2.) deposited upon an insulative substrate 19 as of alumina. The resistors $R_3$ and $R_4$ each have an area of approximately one square centimeter and each provides a resistance of 500 ohms. Resistors $R_3$ and $R_4$ have a relatively large surface-to-mass ratio and are disposed in a closed chamber 21 of an inert material as of teflon.

Temperature compensating resistors 22 are connected in parallel with each of these resistors $R_3$ and $R_4$ and they have a temperature coefficient opposite to that of resistors $R_3$ and $R_4$ so as to render the resistors $R_3$ and $R_4$ relatively insensitive to temperature fluctuations. Heater elements 23 are contained within the chamber 21 in heat exchanging relation with the resistors $R_3$ and $R_4$. The heating elements 23 are connected to a source of power 24 via a reostat 25 and switch 26.

Temperature sensors 27, such as thermistors are disposed in heat exchanging relation with the substrate 19 and resistors $R_3$ and $R_4$. The electrical output representative of the sensed temperature can then be compared with a reference electrical signal representative of a reference temperature to derive an output for controlling the heaters 23 for maintaining the temperature of the resistors $R_3$ and $R_4$ at a desired value. The gas to be analyzed flows through the chamber 21 from a sample input port at 29 to a suction pump 20, not shown.

A filter 31 is connected in series with the sample induction tubing for removing dust and other gaseous components which would otherwise tend to interfere with the measurement to be made. More particularly, when utilizing a gold sensor film $R_3$ for sensing hydrogen sulfide, such film is very sensitive to mercury vapor and thus filter 31 would include a mercury filter for adsorbing the mercury vapor. Such a filter element would comprise, for example, glass wool coated with cadmium.

An ozone generator 32 is also connected into the sample induction tubing for converting oxygen to ozone and introducing the ozone into the sample chamber 21.

In the case for detecting gaseous reduced sulfur compounds including hydrogen sulfide gas, the reduced sulfur compound gas is inducted at port 29, filtered by filter 31 and thence fed into the sample chamber 21. The sulfur compound or hydrogen sulfide interacts with the gold sensing resitor $R_3$ to increase its resistance and thereby unbalance the bridge 12 to produce an output signal $E_0$ at output terminals 17 and 18. In a typical example, the output signal $E_0$ is shown in FIG. 3. More particularly initially the bridge will be linearly unbalanced, i.e., will produce a linear increase in the output signal $E_0$ as a function of the linear accumulation of the sulfur on the sensing resistor $R_3$. However, after the sulfur has accumulated on the sensor resistor $R_3$ to a certain amount, the sensing resistor $R_3$ tends to become less sensitive to further increases in the accumulation of the sulfur. Thus, the output signal $E_0$ tends to saturate as shown at 34. This non-linear or saturation effect can be removed by cleaning the sensing resistor $R_3$ of the accumulated sulfur component. In one embodiment, this is accomplished by closing the heater switch 26 and adjusting the reostat 25 to raise the temperature of the sensing resistor $R_3$ to a temperature of approximately 265 degrees C. in the presence of oxygen, such as that found in air. By heating the sensing film $R_3$ to 265 degrees C. for a few minutes, the sensor $R_3$ can be restored to its linear detection region.

As an alternative to heating the sensing resistor $R_3$ to 265 degrees C. to oxidize and evolve the sulfur component, the sulfur component can be oxidized and evolved by contacting the accumulated sulfur component with ozone produced by the ozone generator 32. The ozone will oxidize and evolve the accumulated sulfur component at room temperature or approximately 20 degrees C. However, it is noted that when the sulfur component is oxidized and evolved at 20 degrees C. by a reaction with ozone that the baseline resistive value of $R_3$ is not totally restored. It is believed this is due to the formation of gold oxide (AuO). However, it is found that when the temperature of the sensing resistor R is raised to approximately 100 degrees C. and the sulfur component reacted with ozone at this temperature that the baseline is restored to zero.

It is believed that the chemical reactions that are occurring on the surface of the gold sensing resistor $R_3$ are as follows:

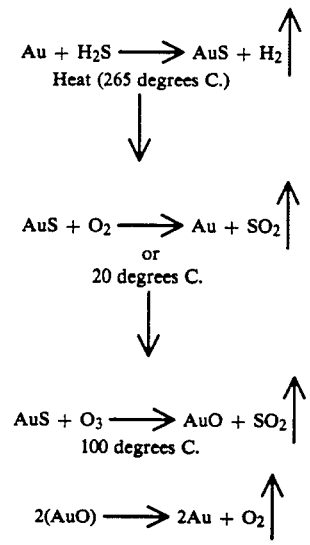

The ozone reaction is much faster than the oxygen reaction at elevated temperature.

Referring now to FIG. 4, there is shown an ozone generator 32 suitable for use in the present invention. More particularly, air or oxygen is admitted into a chamber 36 where it is irradiated by ultra violet radiation, obtained from a u.v. lamp 37, which converts some of the flowing oxygen to ozone.

Referring now to FIG. 6, there is shown an alternative ozone generator 32. In this embodiment, the primary winding 38 of a high voltage step-up transformer 39 is connected to a source of d.c. voltage as of 10 volts via the intermediary of charging resistor 54, as of 100K, and a series connected silicon controlled rectifier 41. A storage capacitor 42 is connected across the input terminals. Periodic turning ON of the silicon controlled rectifier 41 via a trigger pulse at 53 produces periodic bursts of oscillatory high voltage in the secondary winding 43 via transformer 39. The high voltage output current, on the order of many kilovolts is supplied to a central electrode 44 of a corona discharge device 45. More particularly, the corona discharge device includes a grounded shield 46 surrounding an insulative tube 47, as of pyrex, with the electrode or wire 44 extending axially within the tube 47 and centrally of the grounded electrode 46. Air or oxygen is admitted into the discharge device through an entrance port 48 of the tube 47 and is converted, in the corona discharge, into ozone which exits at output port 49.

Referring now to FIG. 6, there is shown an alternative embodiment of the present invention. As is the case with many sensors, the dynamic range of the sensor can be substantially increased by introduction of negative feedback. More particularly, the unbalancing effect of the bridge sensor 12 is detected to derive an output which is fed back to the sensor so that the sensor operates at near null condition. In this manner the sensor is operated in its linear regime, i.e., in its maximum sensitivity or null state, while measuring relatively large effects.

In the case of the gas detector of FIG. 6, the output or unbalance signal $E_0$ obtained from the sensor bridge 12 is fed to the control input of a pulse repetition rate generator 51 which produces an output pulse rate proportional to the magnitude of the bridge unbalance, $E_0$. This in turn controls the rate of ozone production from generator 32 that enters the gas stream to the sensor. The effect of the ozone is to neutralize the hydrogen sulfide affecting the sensor at a rate nearly proportional to the amount of hydrogen sulfide present in the gas or fluid sample, thus maintaining the bridge near its null, or maximum sensitivity point. Since the quantity of ozone evolved is very nearly equivalent to the amount of hydrogen sulfide present, the ozone generator pulse rate or average power requirements is closely related to the hydrogen sulfide concentration over a very broad range and is thus a measure of the sulfur or sulfide concentration.

A similar but slower effect is obtained by controlling the temperature of the sensor via heater elements 22 and the setting of variable temperature controller 54 to effect a thermal decomposition rate of AuS equal to the formation rate, in which case the power required to maintain such a balance, as measured by power meter 55, becomes a measure of the sulfur or hydrogen sulfide in the sampled gas. A combination of both chemical (ozone) and thermal feedback to maintain sensor null has also been found feasible.

The sensor of the present invention is useful, in general, for detecting reduced sulfur compounds in fluids. A reduced sulfur compound is defined as a compound of sulfur with a less electronegative element such as hydrogen. Included within such reduced sulfur compounds are the mercaptans, many of which are used as odorizers added to natural gas. Various reduced sulfur compounds are listed in Table I below together with their relative detection sensitivity as a scale reading for one part per million of the reduced sulfur compound in an inert fluid carrier.

TABLE I

| GAS 1 PPM | | SCALE READING FOR 1 PPM |
|---|---|---|
| ETSH — | Ethyl Mercaptan | 82 |
| DES — | Diethyl Sulfide ($C_2H_5SC_2H_4$) | 2.9 |
| MES — | Methyl Ethyl Sulfide ($CH_3SC_2H_5$) | 1.3 |
|  | Dimethyl Disulfide ($CH_3SSCH_3$) | 133 |
| TMT — | Tetrahydro Thiophene ($CH_4H_8S$) | 9.4 |
| TBM — | T Butyl Mercaptan ($CH_4H_9SH$) | 85 |
| NPM — | N Propyl Mercaptan ($C_3H_7SH$) | 88 |
| IPM — | Isopropyl Mercaptan ($C_3H_7SH$) | 85 |
| DMS — | Dimethyl Sulfide ($CH_3SCH_3$) | 2.3 |
| SBM — | Secondary Butyl Mercaptan ($C_4H_9SH$) | 70 |
|  | Methyl Mercaptan | ≈80 |
|  | Carbon Disulfide | ≈1.5 |
| $H_2S$ — | Hydrogen Sulfide | 250 |

What is claimed is:

1. A method of detecting the presence of a reduced sulfur compound component in a fluid mixture which comprises selectively adsorbing the reduced sulfur compound from the mixture onto a thin layer of a metal having a chemical affinity for the sulfur component;
   detecting the resistance of the layer consequent to the adsorption for detecting the presence of the selected sulfur component; and
   oxidizing and evolving the sulfur component from the metal having the chemical affinity for the sulfur component in the presence of ozone to maintain the sensitivity of the metal to the adsorbed component.

2. The method of claim 1 wherein the metal is one having an affinity for sulfur and a capacity for forming a compound therewith.

3. The method of claim 2 wherein the metal is a noble metal.

4. The method of claim 3 wherein the metal is gold.

* * * * *